(12) United States Patent
Chung et al.

(10) Patent No.: US 11,478,096 B2
(45) Date of Patent: Oct. 25, 2022

(54) FOOD MONITORING SYSTEM

(71) Applicant: KONINKLIJKE PHILIPS N.V., Eindhoven (NL)

(72) Inventors: Wai Kit Chung, Eindhoven (NL); Chi Yu Chen, Eindhoven (NL); Weimin Xiao, Eindhoven (NL); Zhongchi Luo, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 949 days.

(21) Appl. No.: 16/095,527

(22) PCT Filed: Apr. 28, 2017

(86) PCT No.: PCT/EP2017/060305
§ 371 (c)(1),
(2) Date: Oct. 22, 2018

(87) PCT Pub. No.: WO2017/186964
PCT Pub. Date: Nov. 2, 2017

(65) Prior Publication Data
US 2019/0125113 A1 May 2, 2019

(30) Foreign Application Priority Data

Apr. 28, 2016 (WO) ................ PCT/CN2016/080557
Jun. 6, 2016 (EP) ..................................... 16173127

(51) Int. Cl.
*G09B 19/00* (2006.01)
*A47G 23/12* (2006.01)
(Continued)

(52) U.S. Cl.
CPC ......... *A47G 23/12* (2013.01); *G01G 19/4146* (2013.01); *G09B 19/0092* (2013.01); *G16H 20/60* (2018.01)

(58) Field of Classification Search
CPC ............... A47G 23/12; G01G 19/4146; G09B 19/0092; G16H 20/60
See application file for complete search history.

(56) References Cited

U.S. PATENT DOCUMENTS 7,432,454 B1 10/2008 Sze
8,392,124 B2 3/2013 Hyde
(Continued)

FOREIGN PATENT DOCUMENTS

CA 2835878 A1 1/2013
CA 2858566 A1 6/2013
(Continued)

*Primary Examiner* — Thien M Le
(74) *Attorney, Agent, or Firm* — Maschoff Brennan

(57) ABSTRACT

A dining system includes a serving receptacle, an information processor, and utensil(s). Each utensil has an identifier. Each serving receptacle has a measuring system, for measuring an amount of food on the serving receptacle. Each serving receptacle has a reader for reading the identifier of any of the utensils that is brought to a position in which it can remove food from the serving receptacle. Each serving receptacle has a transmitter, for notifying the information processor of a change in the amount of food on the serving receptacle and of an identified utensil that is in a position in which it can remove food from the serving receptacle at a time of the change in the amount of food on the serving receptacle, and the information processor stores information relating to a total quantity of food removed from the serving receptacle by the identified utensil.

13 Claims, 9 Drawing Sheets

(51) Int. Cl.
*G01G 19/414* (2006.01)
*G16H 20/60* (2018.01)

(56) References Cited

U.S. PATENT DOCUMENTS

| | | | |
|---|---|---|---|
| 9,042,596 B2 | 5/2015 | Connor | |
| 9,146,147 B1* | 9/2015 | Bakhsh | A47G 21/02 |
| 9,349,297 B1 | 5/2016 | Ortiz | |
| 2006/0036395 A1 | 2/2006 | Shaya | |
| 2010/0125177 A1* | 5/2010 | Hyde | G09B 19/0092 |
| | | | 708/133 |
| 2010/0125418 A1* | 5/2010 | Hyde | G01G 19/56 |
| | | | 702/19 |
| 2010/0240962 A1* | 9/2010 | Contant | A61B 5/4866 |
| | | | 600/300 |
| 2012/0077154 A1 | 3/2012 | Highet et al. | |
| 2013/0273508 A1* | 10/2013 | Hyde | G09B 19/0092 |
| | | | 434/127 |
| 2013/0336519 A1* | 12/2013 | Connor | G06V 30/142 |
| | | | 382/100 |
| 2014/0347491 A1 | 11/2014 | Connor | |
| 2014/0349257 A1 | 11/2014 | Connor | |
| 2015/0179086 A1* | 6/2015 | Kim | A47G 21/04 |
| | | | 434/260 |
| 2015/0329260 A1* | 11/2015 | Singh | G06Q 10/087 |
| | | | 705/28 |
| 2016/0247118 A1* | 8/2016 | Singh | G06Q 10/087 |

FOREIGN PATENT DOCUMENTS

| | | |
|---|---|---|
| CN | 102799786 A | 8/2011 |
| CN | 201929600 U | 8/2011 |
| WO | 2010070645 A1 | 6/2010 |
| WO | 2015084116 A1 | 6/2015 |

* cited by examiner

FOOD MONITORING SYSTEM

This application is the U.S. National Phase application under 35 U.S.C. § 371 of International Application No. PCT/EP2017/060305, filed on Apr. 28, 2017, which claims the benefit of International Application No. PCT/CN2016/080557 filed Apr. 28, 2016 and International Application No. 16173127.8 filed Jun. 6, 2016. These applications are hereby incorporated by reference herein.

TECHNICAL FIELD

The invention relates to a method and apparatus for monitoring a consumer, and in particular for monitoring the ingestion of food and/or drink by a consumer.

BACKGROUND TO THE INVENTION

Over-eating is the main cause of obesity. In some cases, people are not always consciously aware that they are eating more than their body requires on a daily basis. Often, when over-eating occurs the person does not realise it until there has been a substantial increase in their body weight, and it can be too late to make a small change to their eating habits and improve the situation.

However, with current food intake measuring solutions such as a manual food log, it would be difficult and inconvenient to accurately monitor the nutritional intake for each individual sharing different dishes with other people.

WO2015/084116 provides a food intake monitoring system that is effective for monitoring the food consumed by a single user from one or more receptacle.

From a nutrition/health monitoring and management perspective, it would be useful to be able to measure the food type/weight intake of each individual, in order to monitor the food intake of each meal, either for an individual or shared with others.

SUMMARY OF THE INVENTION

According to a first aspect of the invention there is provided a dining system. The dining system comprises: at least one serving receptacle; an information processor and at least one utensil. Each utensil has an identifier. Each serving receptacle comprises a measuring system, for measuring an amount of food on the serving receptacle. Each serving receptacle has a reader for reading the identifier of any of said utensils that is brought to a position in which it can remove food from the serving receptacle. Each serving receptacle comprises a transmitter, for notifying the information processor of a change in the amount of food on the serving receptacle and of an identified utensil that is in a position in which it can remove food from the serving receptacle at a time of said change in the amount of food on the serving receptacle, and the information processor is configured for storing information relating to a total quantity of food removed from the serving receptacle by the identified utensil.

This dining system is therefore capable of distinguishing between different utensils and therefore between different users and to allocate the food removed from each plate to each different user.

The dining system may further comprise a camera for providing image data of food removed from the serving receptacle at a time of said change in the amount of food on the serving receptacle.

This allows the dining system to recognise the food removed by each user and therefore allows the system to attach nutritional values to the food removed by each utensil.

The information processor may be configured for receiving the image data, determining the type of food removed from the serving receptacle, and storing information relating to the type of food. The user is therefore able to obtain information relating to their food consumption.

The information processor may be cloud based, or locally positioned, or within a smart phone.

The information processor may transmit said information relating to a total quantity of food removed from the serving receptacle by the identified utensil to a user device, wherein the user device is linked to the identified utensil.

By linking the identified utensil to the user device, such as a smart phone, the user of both the device and the utensil may receive nutritional information about the food that they have removed with their specific utensil directly to their device.

In some embodiments, if the reader determines that an identified utensil is in a position in which it can remove food from the serving receptacle for a period of time that is shorter than a threshold time period, any food that is removed from the serving receptacle during this time period will be attributed to the actions of any other utensil identifier that is determined to be in a position in which it can remove food from the serving receptacle during this time period.

This avoids any false identifications of utensils which only came into range of a reader of a serving receptacle whilst passing over the receptacle without removing any food.

In some embodiments, if the reader determines that an identified utensil is in a position in which it can remove food from the serving receptacle for a period of time that is longer than a threshold time period, a change in the amount of food on the serving receptacle during this time is attributed to the utensil removing food from the serving receptacle.

According to another aspect of the invention there is provided a serving receptacle. The serving receptacle comprises a measuring system for measuring an amount of food on the serving receptacle; a reader for reading the identifiers of utensils that are brought to a position in which they can remove food from the receptacle; and a transmitter, for notifying an information processor of a quantity of food removed from the receptacle by an identified utensil.

The serving receptacle may be a plate. The reader may be located at the centre of the serving receptacle such that a recognition distance of the reader is the same as the radius of the serving receptacle.

According to another aspect of the present invention there is provided a utensil comprising a unique identifier for identifying the utensil to a serving receptacle.

The utensil may comprise a visually distinct portion for use in measuring the size of the food being removed by said utensil.

According to another aspect of the invention there is provided a method of monitoring individual food consumption in a group of consumers. The method comprises measuring an amount of food on a serving receptacle; if at least one utensil is used to remove food from the receptacle, wherein the at least one utensil has an identifier; reading the identifier of the at least one utensil; and determining the total weight of food removed from the serving receptacle by the at least one utensil.

The method may further comprise transmitting data relating to the total quantity of food removed from the serving receptacle to an information processor.

If at least two utensils are used to remove food from the receptacle at overlapping times, then the method further may further comprise the information processor estimating the weight of food taken by each utensil.

The estimating step may comprise calculating the size of the food removed by each utensil determining the density of the food removed by each utensil; and multiplying the size by the density to determine the weight of the food removed by each utensil respectively.

According to another aspect of the invention there is provided a computer program product comprising a computer readable medium having computer readable code embodied therein, the computer readable code being configured such that, on execution by a suitable computer or processor, the computer or processor performs the method as described above.

BRIEF DESCRIPTION OF THE DRAWINGS

For a better understanding of the invention, and to show more clearly how it may be carried into effect, reference will now be made, by way of example only, to the accompanying drawings, in which.

DESCRIPTION

It is common that several dishes are served separately on one or more plates that are centrally placed on a dining table which can then be shared by different members of a group.

Figure 1:
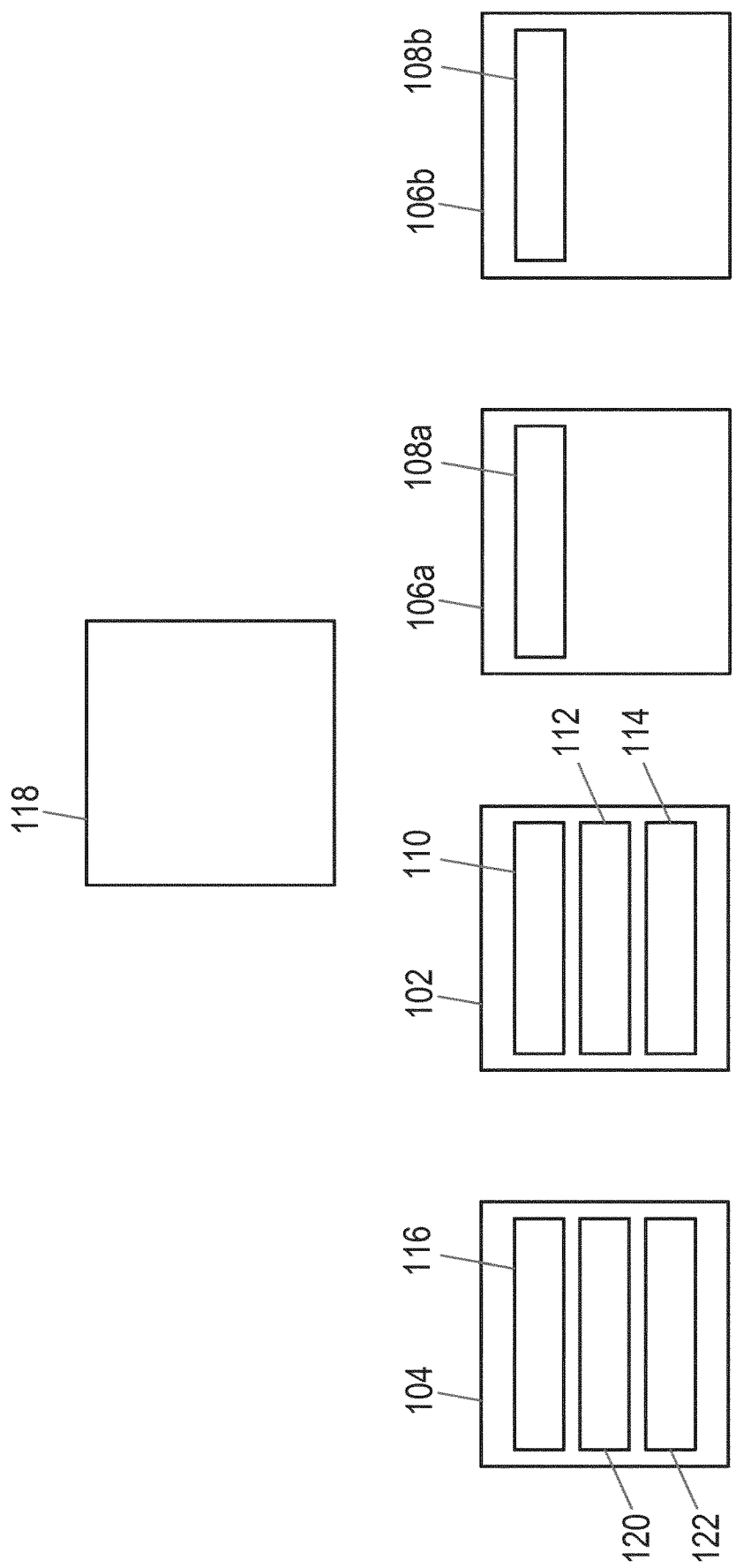
FIG. 1 illustrates a block diagram of a dining system according to embodiments of the invention.

FIG. 1 illustrates a block diagram of a dining system 100 according to embodiments of the invention. The dining system comprises a serving receptacle 102, an information processor 104; at least one utensil 106a, 106b, and a food type recognition element 118.

The utensil 106a comprises an identifier 108a. The identifier 108a can be used to identify the particular utensil 108a to the dining system 100. Equivalently, the utensil 106b comprises a different identifier 108b which can be used to identify the utensil 108b to the dining system 100. In some embodiments the identifier 108a, 108b is a radio-frequency identification (RFID) tag.

The identifiers 108a and 108b may be sealed within the utensils 106a and 106b respectively, so as to not interfere with the food being removed.

The serving receptacle 102 comprises a measuring system 110 for measuring an amount of food on the receptacle. The measuring system may be a scale for measuring weight.

The serving receptacle 102 comprises a reader 112 for reading the identifier 108a, 108b of any of said utensils 106a, 106b when a utensil is brought to a position in which it can remove food from the receptacle 102. In some embodiments, for example, when the utensils include RFID tags, the reader will be an RFID reader.

The serving receptacle 102 may also comprise a transmitter 114, for notifying the information processor 104 of a quantity of food removed from the receptacle 102 by an identified utensil. The transmitter 114 may be wired or wireless.

The information processor 104 is configured for storing information relating to a total quantity of food removed from the receptacle by the identified utensil in a memory 116. It will be appreciated that the information processor may be cloud based, locally mounted or within a smart phone. In the embodiments where the information processor is located within a smart phone there may be a plurality of smart phones each with an individual information processor.

The utensils 106 may be pairs of chopsticks, forks, spoons, serving utensils or any other suitable utensil. The serving receptacles 102 may be plates, bowls serving dishes, or any other suitable serving receptacle.

In this embodiment there is also a food type recognition element 118. This may be implemented using one or more cameras for imaging food on the serving receptacle, and suitable processing means which may be utilised to distinguish between different types of food. In some cases they may be used to distinguish between different types of food on the same serving receptacle.

The information processor 104 comprises a receiver 120 for receiving information from the at least one serving receptacle 102 and the food type recognition element 118. The serving receptacle 102 may send to the information processor 104 data relating to the amount of food removed. For example, the measuring system 110 may calculate a change in the amount of food on the serving receptacle, or may send data relating to amounts of food on the serving receptacle before and after food is removed, allowing the information processor to calculate the change in the amount of food on the serving receptacle. The serving receptacle also sends to the information processor 104 data relating to the identities of an identified utensil that is in a position in which it can remove food from the serving receptacle at a time of said change in the amount of food on the serving receptacle. The food type recognition element may be a camera which sends image data to the information processor 104.

The information processor will then processes the received information in a processor 122 and determine the type of food removed by each utensil and, in some embodiments, the nutritional value of that food. This may be carried out by comparing the images recorded by the one or more cameras to a library of images of different types of food.

Figure 2:
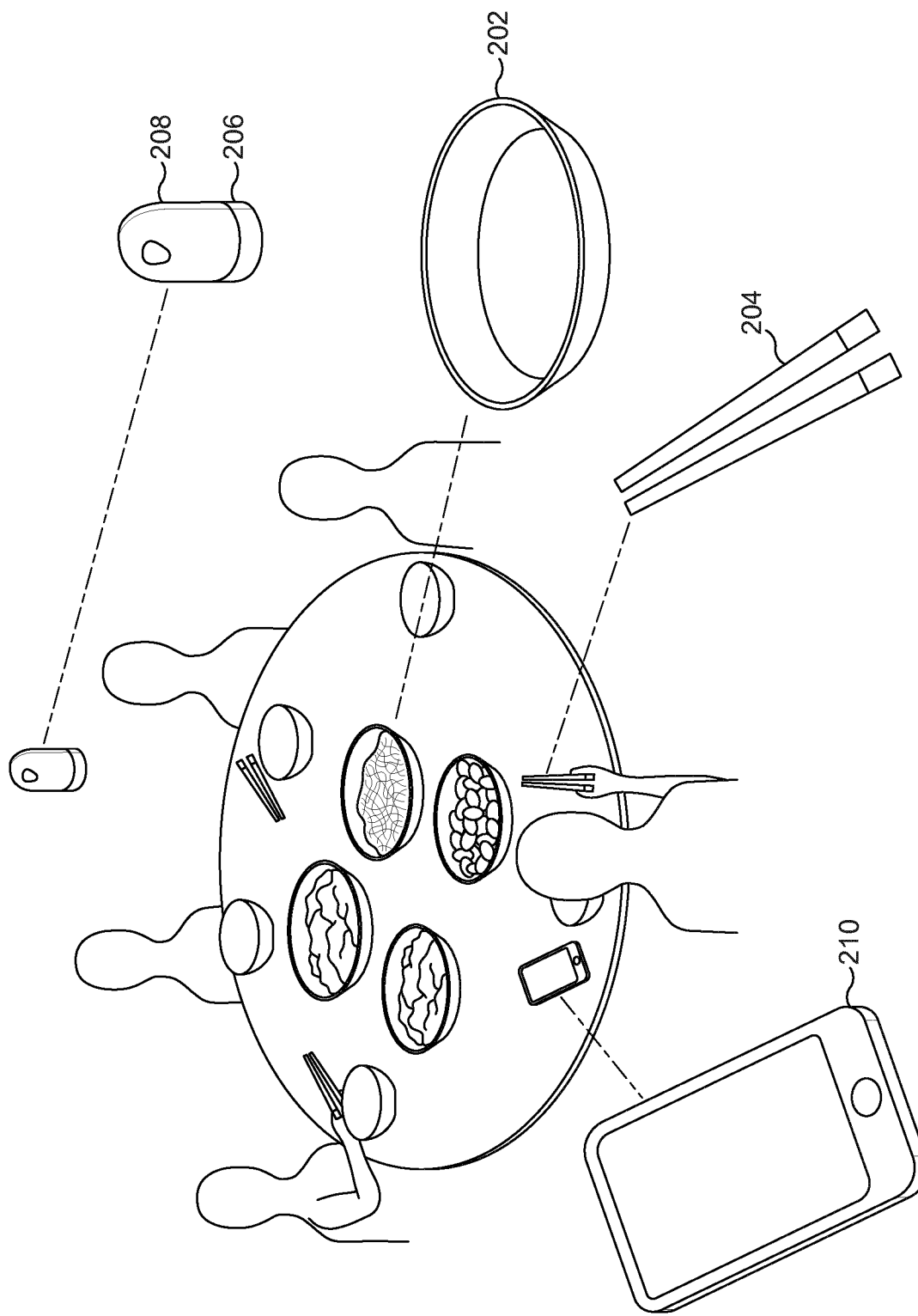
FIG. 2 illustrates a first embodiment of the dining system of FIG. 1.

FIG. 2 illustrates a first embodiment of the dining system of FIG. 1. In this embodiment there are four serving receptacles 102 comprising readers 112, which may be smart plates 202, and five utensils which may be pairs of chopsticks 204. However, it will be appreciated that any type of serving receptacle or utensil may be used. It will also be appreciated that any number of serving receptacles and/or utensils may be used.

In this embodiment, the information processor 104 is within a central hub 206 which also comprises a camera 208. The camera 208 may be used to provide image data of food on each smart plate 202 at a time of said change in the amount of food on the smart plate. This image data may then be sent to the information processor 104 which can determine the type of food being removed by the utensil.

In this embodiment a user device such as a smart phone 210 is also shown. The central hub 206 may be configured to process the data received from the serving receptacles and send the processed data to the smart phone 210.

In particular, in some embodiments, each consumer may have a smart phone 210 or similar user device, which can be linked with their individual utensils 204. In this embodiment, the central hub 206 may only send information to a particular smart phone which relates to a utensil to which it has been linked. In some embodiments more than one utensil may be linked a single user device, for example, in circumstances where a user might use more than one utensil.

Figure 3:
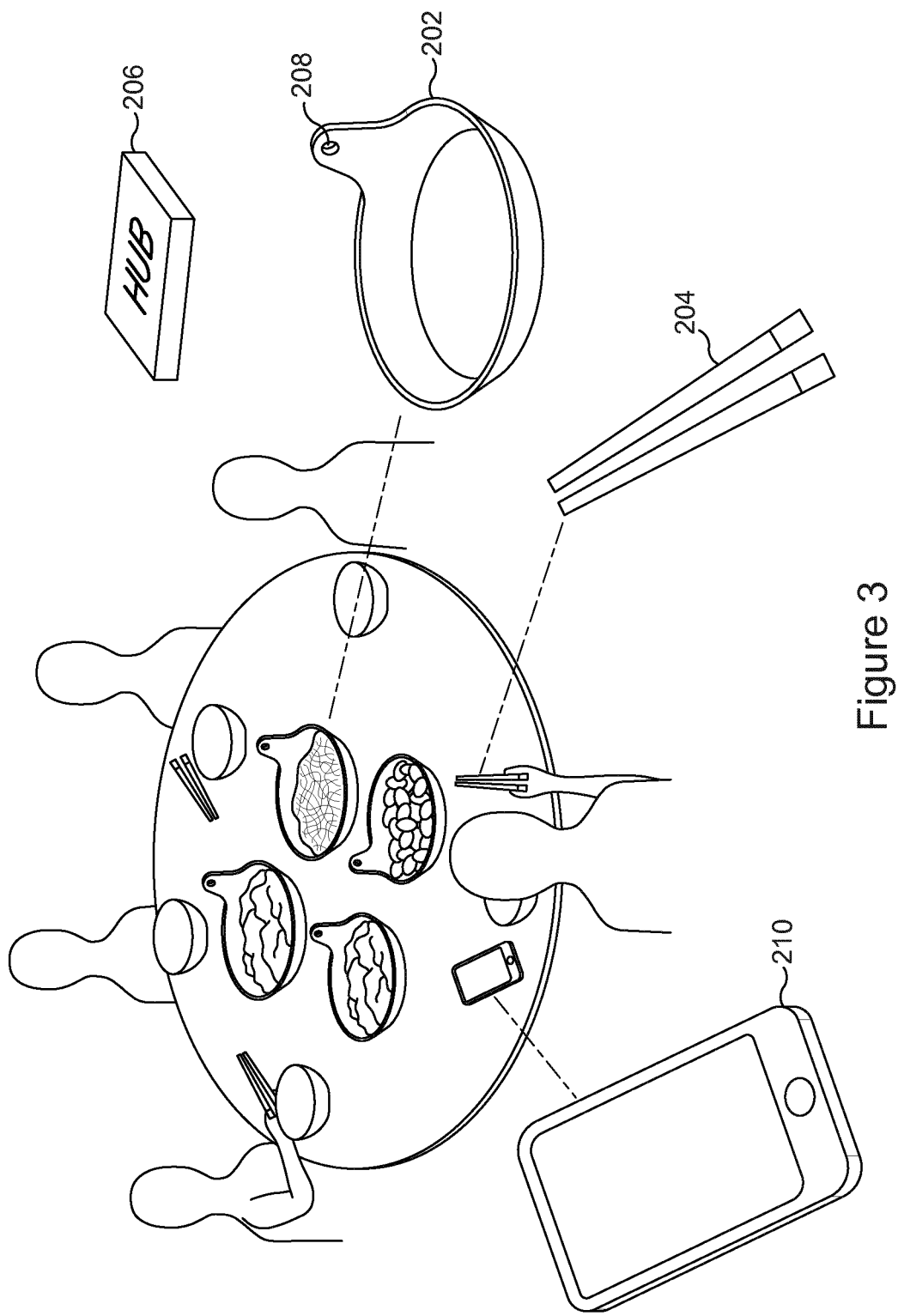
FIG. 3 illustrates another embodiment of the dining system of FIG. 1.

FIG. 3 illustrates another embodiment of the dining system of FIG. 1. Similar features to those of FIG. 2 have been given corresponding reference numerals. Again, in this embodiment there are four serving receptacles 102, which are smart plates 202, and five utensils which in this embodiment are chopsticks 204. It will also be appreciated that any number or type of serving receptacles and/or utensils may be used.

In this embodiment the information processor is contained within a central hub 206 which does not comprise a camera. Instead, each smart plate 202 is provided with an integrated camera 208. The cameras 208 may be used to determine the type of food on each smart plate 202. For example, the cameras may capture image information when a particular smart plate indicates that a utensil is within sensing range. This image information may then be sent to the information processor 104 which can determine the type of food being removed by the utensil.

In this embodiment a smart phone 210 is also shown. The central hub 206 may be configured to process the data received from the serving receptacles and send the processed data to the smart phone.

In particular, in some embodiments, each consumer may have a smart phone or similar user device, which can be linked with their individual utensils. In this embodiment the central hub may only send information to a particular smart phone which relates to a utensil to which it has been linked. In some embodiments more than one utensil may be linked a single user device, for example, in circumstances where a user might use more than one utensil.

Figure 4:
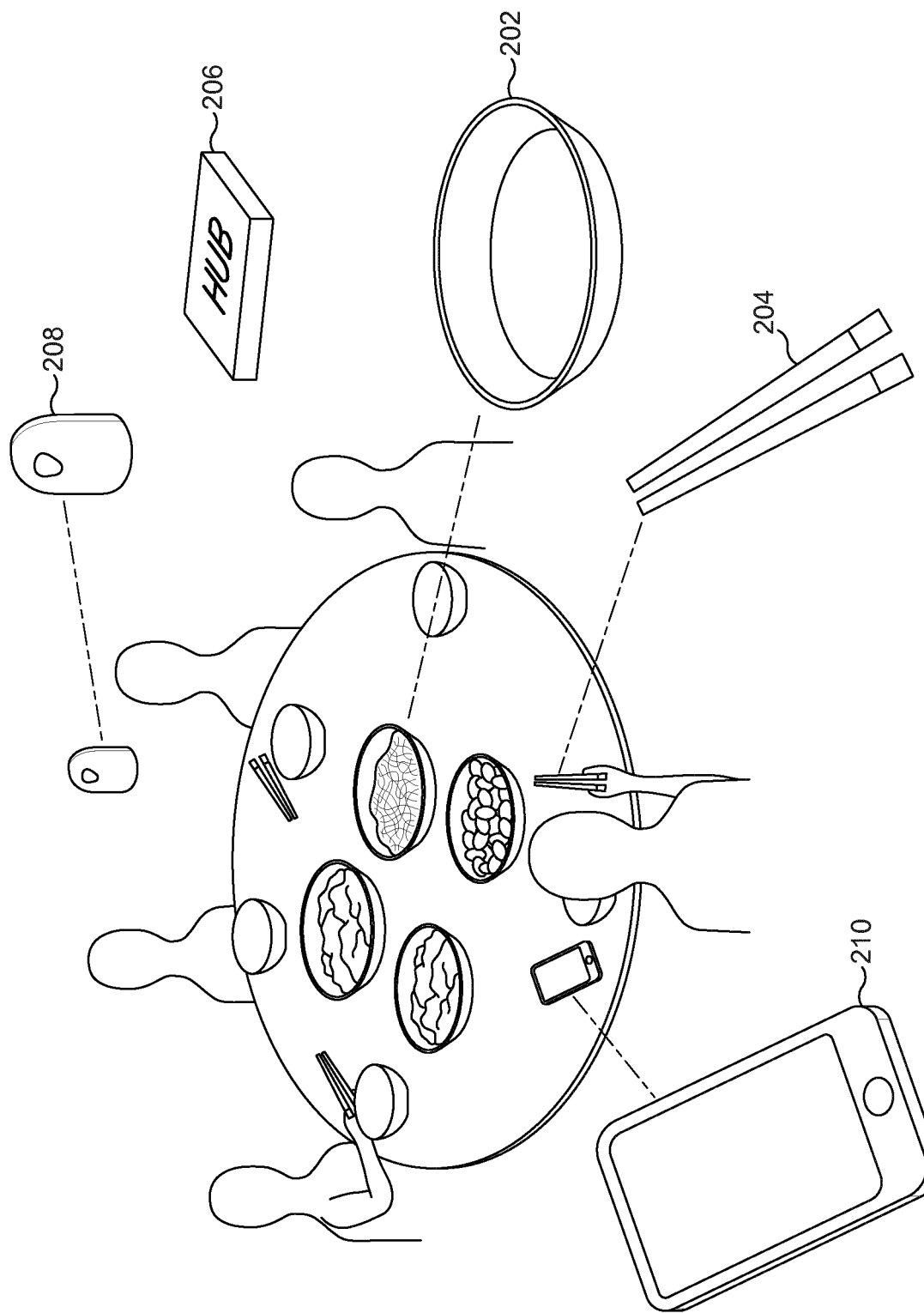
FIG. 4 illustrates an embodiment of the dining system of FIG. 1.

FIG. 4 illustrates an embodiment of the dining system of FIG. 1. Similar features to those of FIG. 2 have been given corresponding reference numerals. Again, in this embodiment there are four serving receptacles 102, which are smart plates 202, and five utensils which are chopsticks 204. However, it will be appreciated that any type of serving receptacle or utensil may be used. It will also be appreciated that any number of serving receptacles and/or utensils may be used.

In this embodiment the information processor is contained within a central hub 206 which does not comprise a camera. Instead, a camera 208 is provided separately. The camera 208 may be used to provide image data of food on each smart plate 202 at a time of a change in the amount of food on the smart plate. This image data may then be sent to the information processor 104 which can determine the type of food being removed by the utensil.

Figure 5:
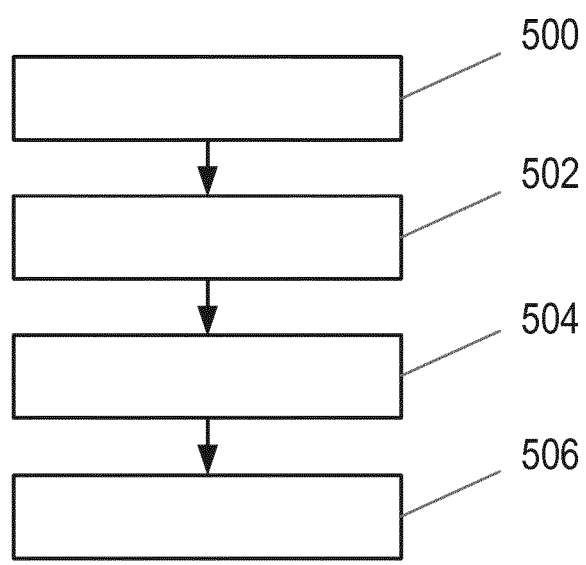
FIG. 5 illustrates a method of using the dining system of any one of FIGS. 1 to 4.

FIG. 5 illustrates a method of using the dining system of any one of FIGS. 1 to 4.

In step 500 a serving receptacle measures an amount of food on the serving receptacle. This measurement may be done continuously or in some embodiments only when a reader in a serving receptacle identifies a particular utensil.

In step 502 it is determined whether at least one utensil is being used to remove food from the receptacle because it has been brought within range of the reader within the serving receptacle, wherein the at least one utensil has an identifier.

In step 504 the serving receptacle reads the identifier of the at least one utensil. For example the reader may be an RFID reader which reads the RFID tag in the utensil in a conventional manner.

In step 506 the serving receptacle determines total weight of food removed from the serving receptacle by the at least one utensil. This may be done by subtracting a weight measurement taken after the utensil has gone out of range from a weight measurement taken before the utensil came within range.

In some embodiments the serving receptacle transmits information containing at least: the identifiers of the utensils, and the amount of food removed by the identified utensils to an information processor.

In some embodiments a camera 208 transmits images of the food removed, during a period when an identified utensil is within range of the reader, to an information processor which determines the type of food removed. For example, the information processor may compare the images received from the camera 208 to a library of images of different food types. Image comparison will then allow the information processor to determine which type of food has been removed. In other embodiments, a specific receptacle may be associated with a general or specific type of food, and this association may be used to simplify identification of the type of food.

Based on the type of food removed and the amount of food removed, nutritional information may be provided by the information processor about the food removed by the utensil. This nutritional information may then be linked to the user of the utensil which was within range of the reader when the food was removed from the receptacle.

In some occasions two consumers may attempt to take food from the same serving receptacle at the same time. In these circumstances, certain procedures may be followed in order to determine how much food has been taken by each consumer.

In some embodiments a rule may be set so that different consumers are not allowed to take food from the same plate simultaneously, in order to avoid the aforementioned scenario.

In other embodiments when two or more consumers take food from the same plate simultaneously, an estimate of the amount of food removed by each consumer can be made by dividing the total amount of food removed by the number of consumers who simultaneously removed food. In this case "simultaneously" can refer to the at least two utensils being within range of the reader in the receptacle at the same time for any period of time. Alternatively, "simultaneously" can refer to any reader response which may indicate that a single measurement of a weight change on the receptacle could be attributed to two different utensils.

Figure 6:
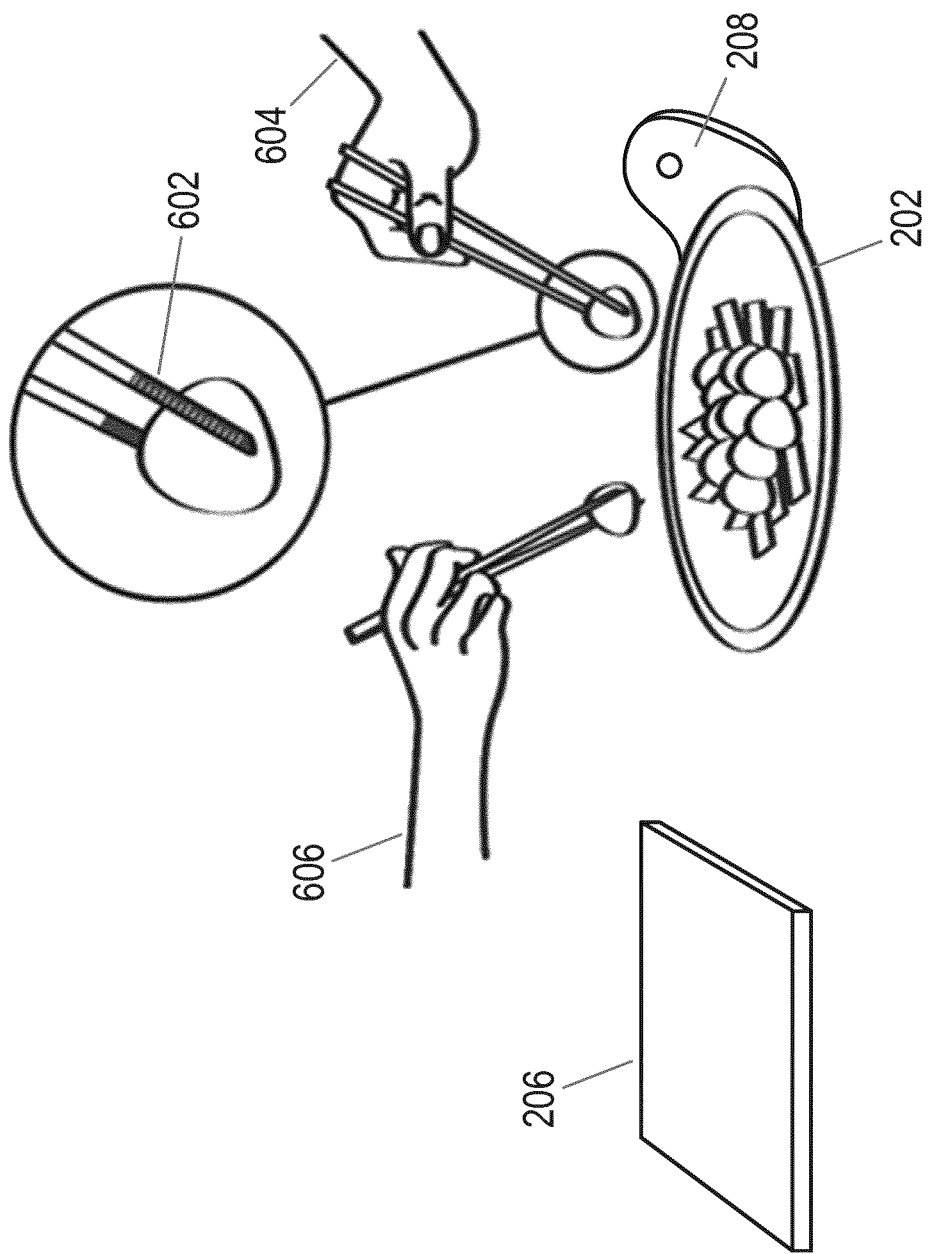
FIG. 6 illustrates a scenario where two consumers, consumer 604 and consumer 606, remove food from the same serving receptacle simultaneously.

In some embodiments, the utensils will be provided with a visibly distinct portion 602 as shown in FIG. 6, which is in some way visually distinguishable from the rest of the utensil. For example, for chopsticks the distinct portion 602 may be a different colour to the rest of the portion, whereas for a fork, the distinct portion 602 may simply be the portion formed by the prongs of the fork. This distinct portion 602 may be for use in measuring the size of the food being removed by said utensil.

FIG. 6 illustrates a scenario where two consumers, consumer 604 and consumer 606, remove food from the same serving receptacle simultaneously. It will be appreciated that more than two users could remove food simultaneously from the same serving receptacle.

In this example consumer 604 removes a piece of beef sized 6 cm$^3$ and consumer 606 removes a piece of carrot sized 4 cm$^3$. The total weight removed recorded by the serving receptacle may be 10 g.

In this embodiment the food weight estimation is based on image recognition and the total weight change. The information regarding food size and food type can be obtained via image analysis. The camera 208, which in this embodiment is integrated into the serving receptacle 202, may provide image data of the food being taken by the respective consumers and transmit this data to the central hub 206, whilst the serving receptacle 202 will also send the total weight change data to the central hub 206, as well as data identifying the utensils.

Figure 7:
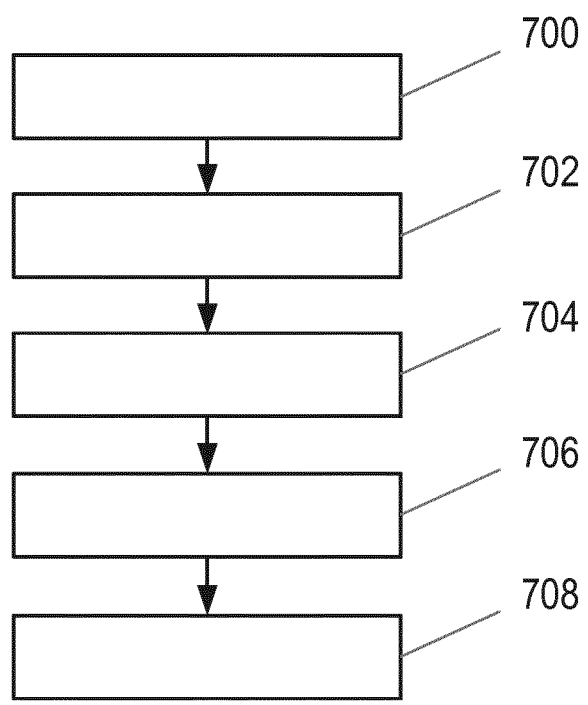
FIG. 7 is a flow chart illustrating the process carried out by a central hub to determine the food weight taken by each consumer in a scenario such as that described in FIG. 6.

FIG. 7 is a flow chart illustrating the process carried out by a central hub to determine the food weight taken by each consumer in a scenario such as that described in FIG. 6.

When the central hub receives data indicating that at least two utensils have been identified during a weight change recorded by the receptacle, the following method may be used.

In step 700 the central hub receives the image data from the camera 208, and the weight change data from the serving receptacle 202 along with the data identifying the utensils.

In step 702, the central hub determines the size of the piece of food taken by each person or utensil. This may be done through image analysis by comparing the piece of food to the highlighted portion 602 of the utensil being used by each person.

In step 704, the central hub determines the density of the food taken by each person. This may be done through image analysis to determine the type of food, and using a database to look up an estimate of the density of that food type. For example, in the scenario described in FIG. 6, the beef may have a density of 1.15 g/cm$^3$ and the carrot may have a density of 1.03 g/cm$^3$.

In step 706, the central hub then calculates the food weight taken by each person respectively. This may be done by multiplying the sizes of the pieces of food removed by each person calculated in step 702 by the respective densities determined in step 704. For example, in the scenario described with reference to FIG. 6, the calculated weight for the food removed by consumer 604 would be 1.15 g/cm$^3$×6 cm$^3$=6.9 g.

The calculated weight for the food removed by consumer 606 would be 1.03 g/cm$^3$×4 cm$^3$=4.12 g.

In step 708 the central hub then adjusts the food weight calculated in step 706. This may be done by comparing the sum of the weights calculated in step 706 to the total weight change data received from the serving receptacle in step 700. In the scenario described with reference to FIG. 6, the total weight change is 10 g. Therefore the adjusted weight for the food removed by person A may be calculated as follows:

$$(10 \text{ g} \times 6.9 \text{ g})/(6.9 \text{ g} + 4.12 \text{ g}) = 6.26 \text{ g}.$$

Equivalently, the adjusted weight for the food removed by person B may be calculated as follows:

$$(10 \text{ g} \times 4.12 \text{ g})/(6.9 \text{ g} + 4.12 \text{ g}) = 3.74 \text{ g}.$$

Figure 8:
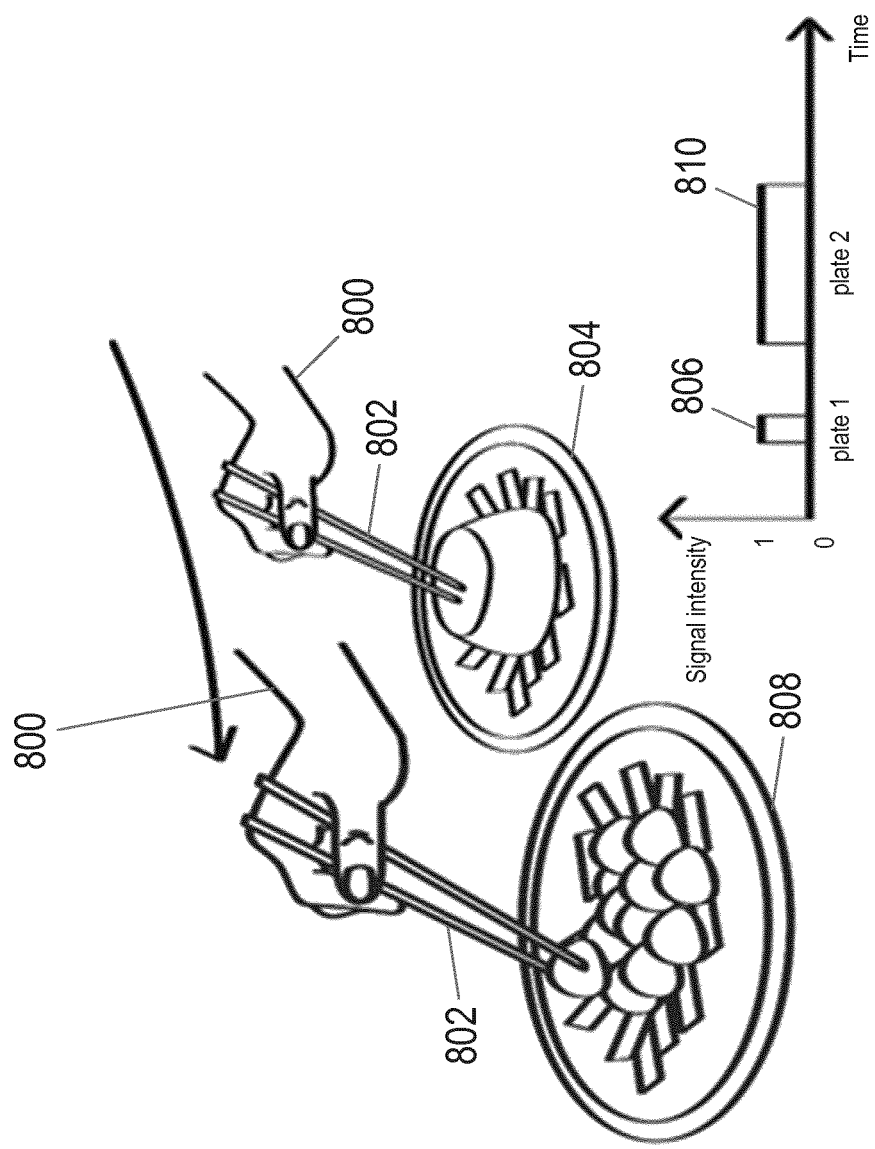
FIG. 8 illustrates the response of the signal intensity detected by the readers of two different serving receptacles.

FIG. 8 illustrates the response of the signal intensity detected by the readers of two different serving receptacles.

As the consumer 800 passes the utensil 802 over the serving receptacle 804, a signal 806 is recorded as the reader in serving receptacle 804 detects the identifier in the utensil 802. However, in this scenario the consumer continues to move his utensil over the serving receptacle 804 to the serving receptacle 808, where he pauses to remove some food. The signal 806 is therefore short (for example, shorter than a threshold time period, which may for example be one second, or any time period that is judged to be insufficient to remove food from the receptacle), and any food removed from the serving receptacle 804 during this time will be attributed to the actions of any other utensil identifier detected by the serving receptacle 804 during this time. Therefore, due to the short duration of the signal 806, the utensil 802 will not be counted as an identified utensil by the reader in the receptacle 804 at this time. In contrast, the signal 810 produced when the utensil 802 is over the serving receptacle 808, is long enough to be representative of a consumer removing food from the serving receptacle 808, and hence any weight change recorded by the serving receptacle 808, is attributed to the removal of food by the utensil 802.

Figure 9:
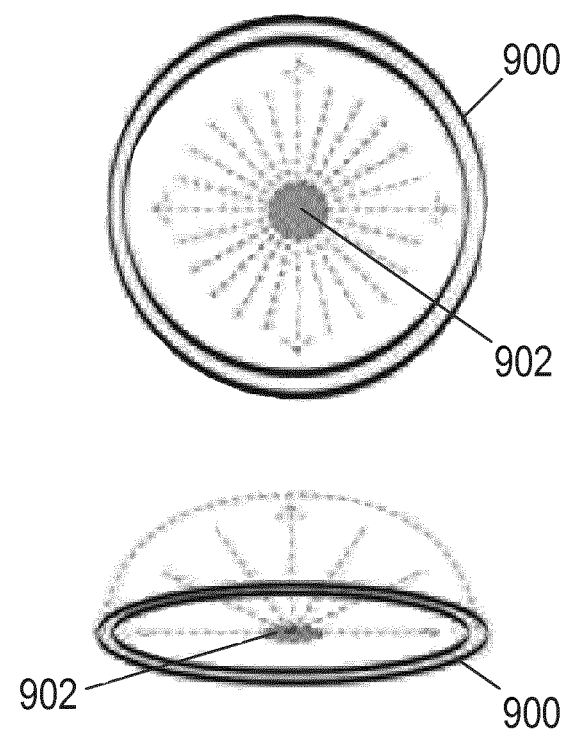
FIG. 9 illustrates a serving receptacle.

In order to prevent any incorrect recognition, the identifier, for example, an RFID reader, may be located at the centre part of a serving receptacle. In some embodiments, such as shown in FIG. 9 the serving receptacle is a smart plate 900, which may be in the form of a plate, dish, bowl or the like, with an RFID reader 902 located at the centre such that the recognition distance is the same as the radius of the smart plate.

There is therefore provided a system for monitoring the ingestion of food by a consumer.

The invention claimed is:

1. A dining system, comprising:
   at least one serving receptacle;
   an information processor; and
   multiple utensils,
   wherein each utensil of the multiple utensils has an identifier, and
   wherein each serving receptacle comprises:
   a measuring system, for measuring an amount of food on a serving receptacle,
   a reader for reading the identifier of any of said multiple utensils that are brought to a position in which it can remove the food from the serving receptacle,
   a transmitter, for notifying the information processor of a change in the amount of food on the serving receptacle and of an identified utensil that is in a position in which it can remove food from the serving receptacle at a time of said change in the amount of food on the serving receptacle, and
   wherein the information processor is configured for storing information relating to a total quantity of food removed from the serving receptacle by the identified utensil.

2. A dining system as claimed in claim 1, further comprising a camera to provide image data of food removed from the serving receptacle at a time of said change in the amount of food on the serving receptacle.

3. A dining system as claimed in claim 2, wherein the information processor is configured to receive the image data, determine the type of food removed from the serving receptacle, and store information relating to the type of food.

4. A dining system as claimed in claim 1, wherein the information processor is cloud based, or
   wherein the information processor is locally positioned, or
   wherein the information processor is within a smart phone.

5. A dining system as claimed in 1, wherein the information processor transmits said information relating to a total quantity of food removed from the serving receptacle by the identified utensil to a user device, wherein the user device is linked to the identified utensil.

6. A dining system as claimed in claim 1, wherein if the reader determines that the identified utensil is in a position in which it can remove food from the serving receptacle for a period of time that is shorter than a threshold time period, any food that is removed from the serving receptacle during this time period will be attributed to actions of any other utensil identifier that is determined to be in a position in which it can remove food from the serving receptacle during this time period.

7. A dining system as claimed in claim 1, wherein if the reader determines that the identified utensil is in a position in which it can remove the food from the serving receptacle for a period of time that is longer than a threshold time period, a change in the amount of food on the serving receptacle during this time is attributed to a utensil removing the food from the serving receptacle.

8. A serving receptacle comprising:
a measuring system for measuring an amount of food on the serving receptacle;
a reader for reading identifiers of multiple utensils that are brought to a position in which they can remove food from the receptacle; and
a transmitter, for notifying an information processor of a quantity of food removed from the receptacle by an identified utensil.

9. A serving receptacle as claimed in claim 8, wherein the serving receptacle is a plate, a dish, a bowl or the like, and the reader is located at a centre of the serving receptacle such that a recognition distance of the reader is same as radius of the serving receptacle.

10. A method of monitoring individual food consumption in a group of consumers, comprising:
measuring an amount of food on a serving receptacle;
if multiple utensils are used to remove food from the receptacle, wherein each utensil has an identifier;
reading identifiers of the multiple utensils;
determining the amount of food removed from the serving receptacle by each utensil; and
transmitting data relating to the amount of food removed from the serving receptacle to an information processor.

11. A method as claimed in claim 10, further comprising; if at least two utensils are used to remove food from the receptacle at overlapping times, then the method further comprises estimating weight of food taken by each utensil by the information processor.

12. A method as claimed in claim 11, wherein said estimating step comprises:
calculating a size of the food removed by each utensil;
determining density of the food removed by each utensil; and
multiplying the size by the density to determine the weight of the food removed by each utensil, respectively.

13. A computer program product comprising a computer readable medium having computer readable code embodied therein, the computer readable code being configured such that, on execution by a processor, the processor performs the method of claim 10.

* * * * *